(12) United States Patent
Ravensbergen et al.

(10) Patent No.: US 8,613,321 B2
(45) Date of Patent: Dec. 24, 2013

(54) BOTTOM HOLE ASSEMBLY WITH PORTED COMPLETION AND METHODS OF FRACTURING THEREWITH

(75) Inventors: John Edward Ravensbergen, DeWinton (CA); Lyle E. Laun, Calgary (CA)

(73) Assignee: Baker Hughes Incorporated, Houston, TX (US)

( * ) Notice: Subject to any disclaimer, the term of this patent is extended or adjusted under 35 U.S.C. 154(b) by 384 days.

(21) Appl. No.: 12/842,099

(22) Filed: Jul. 23, 2010

(65) Prior Publication Data

US 2011/0174491 A1  Jul. 21, 2011

Related U.S. Application Data

(60) Provisional application No. 61/228,793, filed on Jul. 27, 2009.

(51) Int. Cl.
*E21B 43/26* (2006.01)
*E21B 33/12* (2006.01)
*E21B 28/00* (2006.01)

(52) U.S. Cl.
USPC ............... 166/308.1; 166/386; 166/177.5

(58) Field of Classification Search
USPC ............... 166/308.1, 177.5, 19, 319, 386; 285/333
See application file for complete search history.

(56) References Cited

U.S. PATENT DOCUMENTS

| 2,187,483 | A | 1/1940 | Baker |
| 2,189,702 | A | 2/1940 | Burt |
| 2,307,662 | A | 1/1943 | Baylor |
| 4,088,191 | A | 5/1978 | Hutchison |
| 4,257,484 | A | 3/1981 | Whitley |
| 4,260,017 | A | 4/1981 | Nelson |
| 4,312,406 | A | 1/1982 | McLaurin et al. |

(Continued)

FOREIGN PATENT DOCUMENTS

| CA | 2210103 A1 | 5/1998 |
| CA | 2322075 A1 | 4/2001 |

(Continued)

OTHER PUBLICATIONS

Office Action dated Jun. 29, 2012 issued in related Canadian Patent Application No. 2,711,329.

(Continued)

*Primary Examiner* — Daniel P Stephenson
*Assistant Examiner* — Michael Wills, III
(74) *Attorney, Agent, or Firm* — Parsons Behle & Latimer

(57) ABSTRACT

A ported completion and method for use in fracturing multi-zone wells. A casing assembly having a plurality of casing lengths and one or more collars positioned so as to couple together the casing lengths. The collars may be a tubular body having an inner flow path, one or more fracture ports configured to provide fluid communication between an outer surface of the collar and the inner flow path, one or more valve holes intersecting the fracture ports, one or more valve vent holes positioned to provide fluid communication between the valve holes and the inner flow path, and one or more valves positioned in the valve holes for opening and closing the fracture ports. The valves are configured to open when a pressure differential is created between the fracture ports and the valve vent holes. The valve vent hole may be an annulus around the perimeter of the tubular body.

40 Claims, 7 Drawing Sheets

(56) References Cited

U.S. PATENT DOCUMENTS

| | | | |
|---|---|---|---|
| 4,330,039 | A | 5/1982 | Vann et al. |
| 4,429,747 | A | 2/1984 | Williamson |
| 5,358,048 | A | 10/1994 | Brooks et al. |
| 5,417,291 | A | 5/1995 | Leising |
| 5,443,124 | A | 8/1995 | Wood et al. |
| 5,513,703 | A * | 5/1996 | Mills et al. .................. 166/55.1 |
| 6,024,173 | A | 2/2000 | Patel et al. |
| 6,292,242 | B1 * | 9/2001 | VanderPloeg et al. ........ 349/118 |
| 6,513,595 | B1 | 2/2003 | Freiheit |
| 6,832,654 | B2 * | 12/2004 | Ravensbergen et al. ... 166/308.1 |
| 6,883,610 | B2 * | 4/2005 | Depiak ...................... 166/308.1 |
| 7,066,264 | B2 * | 6/2006 | Bissonnette et al. ....... 166/305.1 |
| 7,124,824 | B2 | 10/2006 | Turner et al. |
| 7,249,633 | B2 * | 7/2007 | Ravensbergen et al. ...... 166/301 |
| 7,387,165 | B2 * | 6/2008 | Lopez de Cardenas et al. ............................ 166/313 |
| 7,556,102 | B2 | 7/2009 | Gomez |
| 7,748,463 | B2 | 7/2010 | Revheim |
| 7,789,163 | B2 * | 9/2010 | Kratochvil et al. ........... 166/387 |
| 7,810,570 | B2 * | 10/2010 | Collins et al. ............. 166/308.1 |
| 7,823,633 | B2 * | 11/2010 | Hartwell ..................... 166/66.6 |
| 7,861,774 | B2 * | 1/2011 | Fehr et al. .................... 166/191 |
| 7,861,788 | B2 * | 1/2011 | Tips et al. .................... 166/319 |
| 2003/0019628 | A1 | 1/2003 | Ravensbergen |
| 2003/0127227 | A1 | 7/2003 | Fehr |
| 2004/0238173 | A1 | 12/2004 | Bissonnette et al. |
| 2005/0000693 | A1 | 1/2005 | Ravensbergen |
| 2005/0072577 | A1 | 4/2005 | Freeman |
| 2005/0126787 | A1 | 6/2005 | Gomez |
| 2006/0000620 | A1 * | 1/2006 | Hamilton ...................... 166/387 |
| 2006/0081380 | A1 | 4/2006 | Hoffman |
| 2006/0124310 | A1 | 6/2006 | Lopez de Cardenas |
| 2006/0231253 | A1 | 10/2006 | Vilela et al. |
| 2006/0243435 | A1 | 11/2006 | Faul |
| 2007/0272411 | A1 | 11/2007 | Lopez de Cardenas |
| 2008/0210431 | A1 | 9/2008 | Johnson et al. |
| 2008/0236819 | A1 | 10/2008 | Foster |
| 2009/0014168 | A1 * | 1/2009 | Tips et al. ........................ 166/73 |
| 2009/0044944 | A1 * | 2/2009 | Murray et al. ............. 166/308.1 |
| 2009/0084553 | A1 | 4/2009 | Rytlewski et al. |
| 2010/0089587 | A1 * | 4/2010 | Stout ............................ 166/319 |
| 2010/0263873 | A1 * | 10/2010 | Turner et al. ............... 166/308.1 |
| 2011/0155377 | A1 * | 6/2011 | Laun ............................ 166/308.1 |
| 2011/0308817 | A1 * | 12/2011 | Ravensbergen .............. 166/382 |
| 2012/0111566 | A1 | 5/2012 | Sherman et al. |

FOREIGN PATENT DOCUMENTS

| | | | |
|---|---|---|---|
| CA | 2385795 | A1 | 4/2001 |
| CA | 2397460 | A1 | 8/2001 |
| CA | 2375045 | A1 | 9/2002 |
| CA | 2381620 | | 10/2002 |
| CA | 2392277 | A1 | 12/2002 |
| CA | 2535940 | A1 | 8/2006 |
| CA | 2623100 | A1 | 3/2007 |
| CA | 2559815 | A1 | 9/2007 |
| CA | 2622044 | | 9/2008 |
| CA | 2641778 | | 4/2010 |
| CA | 2688106 | A1 | 7/2010 |
| CA | 2693676 | | 7/2010 |
| CA | 2670218 | | 12/2010 |
| CA | 2711329 | | 1/2011 |
| CA | 2738907 | | 7/2011 |
| EP | 0581533 | A2 | 2/1994 |
| WO | WO2004063527 | A1 | 7/2004 |
| WO | WO2008091345 | A1 | 7/2008 |

OTHER PUBLICATIONS

Office Action issued in corresponding Canadian Patent Application No. 2,711,329, dated Mar. 17, 2011.
Baker Hughes Catalog Flow Control Systems dated 2002, pp. 58 and 61.
Office Action dated Nov. 1, 2012, issued in Canadian Patent application No. 2,711,329.
Office Action issued in Canadian Patent Application No. 2711329 and dated Sep. 6, 2011.
Office Action issued in Canadian Patent Application No. 2711329 and dated Mar. 19, 2012.
Protest filed in Canadian Patent Application No. 2711329 dated Feb. 10, 2012.
Office Action issued in Canadian Patent Application No. 2730695 dated Apr. 27, 2011.
Notice of Protest issued in Canadian Patent Application No. 2730695 dated Feb. 24, 2012.
Protest filed Under S 34.1 in Canadian Patent Application No. 2730695 dated Feb. 23, 2012.
Office Action issued in Canadian Patent Application No. 2730695 dated Apr. 5, 2012.
Protest and Prior Art Submission in Canadian Patent Application No. 2730695 filed on Aug. 16, 2012.
Notice of Protested filed in Canadian Patent Application No. 2730695 dated Aug. 24, 2012.
Office Action issued in Canadian Patent Application No. 2781721 dated Sep. 25, 2012.
Office Action issued in Canadian Patent Application No. 2711329 dated Jun. 29, 2012.
Notice of Protest issued in Canadian Patent Application No. 2711329 dated Feb. 13, 2012.
Office Action dated Feb. 21, 2013, issued in Canadian Patent Application No. 2,781,721.
Protest and Prior Art Submission dated Mar. 5, 2013, filed in Canadian Patent Application No. 2,730,695.
ISR—WO dated Apr. 25, 2013 in Application No. PCT/US2011/066185.
Office Action dated May 10, 2013 issued in U.S. Appl. No. 12/971,932.
Office Action dated Dec. 19, 2012, issued in Canadian Patent application No. 2,746,522.
International Search Report dated Apr. 4, 2013 issued in PCT/US2011/065212.
International Search Report dated Apr. 11, 2013 issued in PCT/US2012/051679.
Office Action dated Jan. 30, 2013, issued in Canadian Patent application No. 2,730,695.
Canadian Office Action dated Sep. 13, 2013 issued in CA 2,746,522.

* cited by examiner

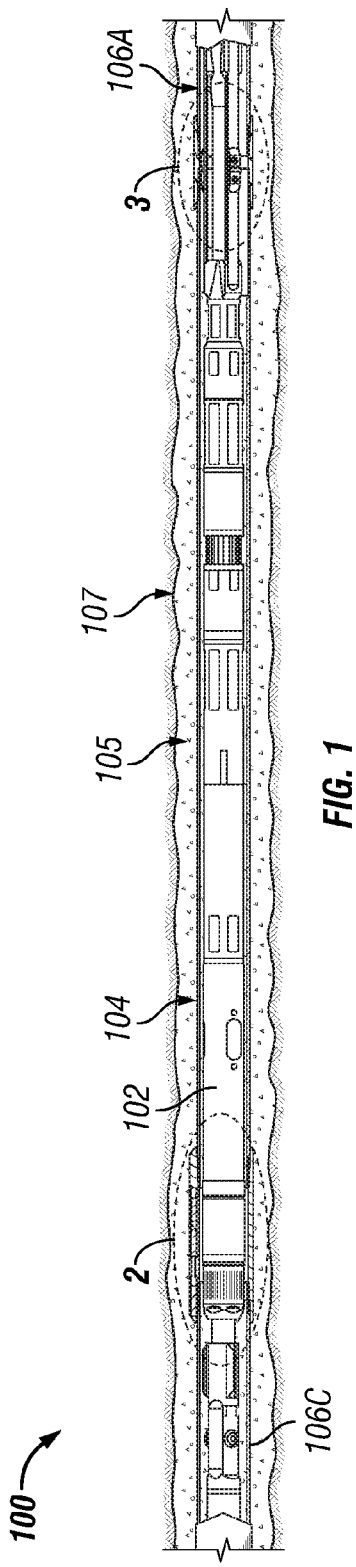
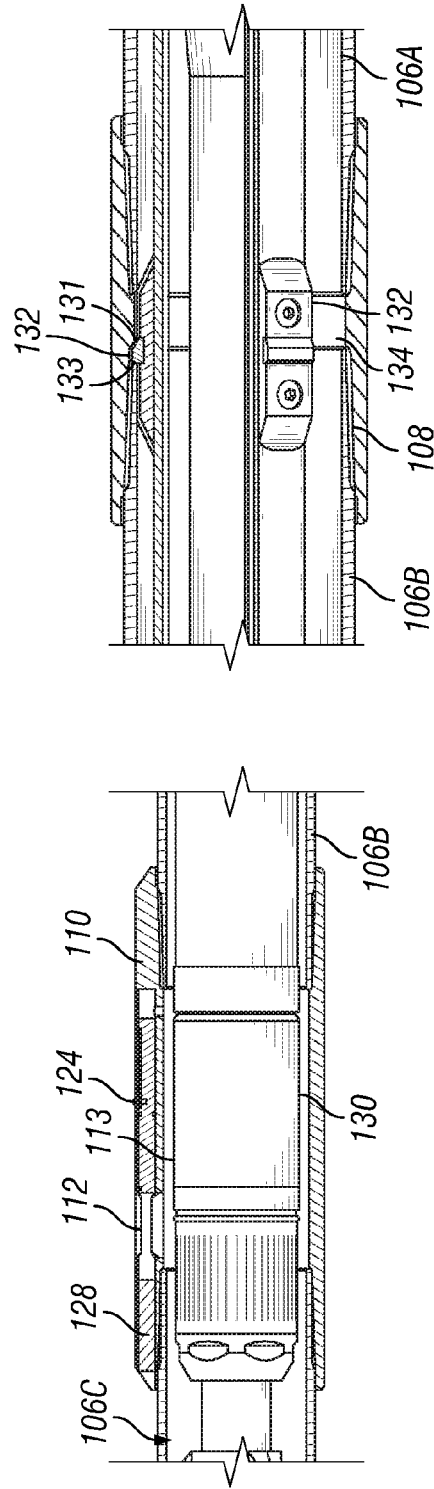
FIG. 1
FIG. 2
FIG. 3

BOTTOM HOLE ASSEMBLY WITH PORTED COMPLETION AND METHODS OF FRACTURING THEREWITH

RELATED APPLICATIONS

The present disclosure claims the benefit of U.S. Provisional Patent Application No. 61/228,793 entitled "BOTTOM HOLE ASSEMBLY WITH PORTED COMPLETION AND METHODS OF FRACTURING THEREWITH" by John Edward Ravensbergen filed on Jul. 27, 2009, which is hereby incorporated by referenced in its entirety.

BACKGROUND

1. Field of the Disclosure

The present disclosure relates generally to a downhole tool for use in oil and gas wells, and more specifically, to a ported completion that can be employed for fracturing in multi-zone wells.

2. Description of the Related Art

Oil and gas well completions are commonly performed after drilling hydrocarbon producing wellholes. Part of the completion process includes running a well casing assembly into the well. The casing assembly can include multiple lengths of tubular casing attached together by collars. A standard collar can be, for example, a relatively short tubular or ring structure with female threads at either end for attaching to male threaded ends of the lengths of casing. The well casing assembly can be set in the wellhole by various techniques. One such technique includes filling the annular space between the wellhole and the outer diameter of the casing with cement.

After the casing is set in the well hole, perforating and fracturing operations can be carried out. Generally, perforating involves forming openings through the well casing and into the formation by commonly known devices such as a perforating gun or a sand jet perforator. Thereafter, the perforated zone may be hydraulically isolated and fracturing operations are performed to increase the size of the initially-formed openings in the formation. Proppant materials are introduced into the enlarged openings in an effort to prevent the openings from closing.

More recently, techniques have been developed whereby perforating and fracturing operations are performed with a coiled tubing string. One such technique is known as the Annular Coil Tubing Fracturing Process, or the ACT-Frac Process for short, disclosed in U.S. Pat. Nos. 6,474,419, 6,394,184, 6,957,701, and 6,520,255, each of which is hereby incorporated by reference in its entirety. To practice the techniques described in the aforementioned patents, the work string, which includes a bottom hole assembly (BHA), generally remains in the well bore during the fracturing operation(s).

One method of perforating, known as the sand jet perforating procedure, involves using a sand slurry to blast holes through the casing, the cement and into the well formation. Then fracturing can occur through the holes. One of the issues with sand jet perforating is that sand from the perforating process can be left in the well bore annulus and can potentially interfere with the fracturing process. Therefore, in some cases it may be desirable to clean the sand out of the well bore, which can be a lengthy process taking one or more hours per production zone in the well. Another issue with sand jet perforating is that more fluid is consumed to cut the perforations and either circulate the excess solid from the well or pump the sand jet perforating fluid and sand into the zone ahead of and during the fracture treatment. Demand in industry is going toward more and more zones in multi-zone wells, and some horizontal type wells may have 40 zones or more. Cleaning the sand from such a large number of zones can add significant processing time, require the excessive use of fluids, and increase the cost. The excessive use of fluids may also create environmental concerns. For example, the process requires more trucking, tankage, and heating and additionally, these same requirements are necessary when the fluid is recovered from the well.

Well completion techniques that do not involve perforating are known in the art. One such technique is known as packers-plus-style completion. Instead of cementing the completion in, this technique involves running open hole packers into the well hole to set the casing assembly. The casing assembly includes ported collars with sleeves. After the casing is set in the well, the ports can be opened by operating the sliding sleeves. Fracturing can then be performed through the ports.

For multi-zone wells, multiple ported collars in combination with sliding sleeve assemblies have been employed. The sliding sleeves are installed on the inner diameter of the casing and/or sleeves and can be held in place by shear pins. In some designs, the bottom most sleeve is capable of being opened hydraulically by applying a differential pressure to the sleeve assembly. After the casing with ported collars is installed, a fracturing process is performed on the bottom most zone of the well. This process may include hydraulically sliding sleeves in the first zone to open ports and then pumping the fracturing fluid into the formation through the open ports of the first zone. After fracturing the first zone, a ball is dropped down the well. The ball hits the next sleeve up from the first fractured zone in the well and thereby opens ports for fracturing the second zone. After fracturing the second zone, a second ball, which is slightly larger than the first ball, is dropped to open the ports for fracturing the third zone. This process is repeated using incrementally larger balls to open the ports in each consecutively higher zone in the well until all the zones have been fractured. However, because the well diameter is limited in size and the ball sizes are typically increased in quarter inch increments, this process is limited to fracturing only about 11 or 12 zones in a well before ball sizes run out. In addition, the use of the sliding sleeve assemblies and the packers to set the well casing in this method can be costly. Further, the sliding sleeve assemblies and balls can significantly reduce the inner diameter of the casing, which is often undesirable. After the fracture stimulation treatment is complete, it is often necessary to mill out the balls and ball seats from the casing.

Another method that has been employed in open-hole wells (that use packers to fix the casing in the well) is similar to the packers-plus-style completion described above, except that instead of dropping balls to open ports, the sleeves of the subassemblies are configured to be opened mechanically. For example, a shifting tool can be employed to open and close the sleeves for fracturing and/or other desired purposes. As in the case of the packers-plus-style completion, the sliding sleeve assemblies and the packers to set the well casing in this method can be costly. Further, the sliding sleeve assemblies can undesirably reduce the inner diameter of the casing. In addition, the sleeves are prone to failure due to high velocity sand slurry erosion and/or sand interfering with the mechanisms.

Another technique for fracturing wells without perforating is disclosed in co-pending U.S. patent application Ser. No. 12/826,372 entitled "JOINT OR COUPLING DEVICE INCORPORATING A MECHANICALLY-INDUCED WEAK POINT AND METHOD OF USE," filed Jun. 29, 2010, by Lyle E. Laun, which is incorporated by reference herein in its entirety.

The present disclosure is directed to overcoming, or at least reducing the effects of, one or more of the issues set forth above.

SUMMARY OF THE DISCLOSURE

The following presents a summary of the disclosure in order to provide an understanding of some aspects disclosed herein. This summary is not an exhaustive overview, and it is not intended to identify key or critical elements of the disclosure or to delineate the scope of the invention as set forth in the appended claims.

One embodiment of the present disclosure is a wellbore completion that includes a casing assembly having a plurality of casing lengths and one or more collar assemblies positioned so as to couple together the casing lengths. The collar assemblies, herein after referred also referred to as a collar, comprise a tubular body having an inner flow path, one or more fracture ports configured to provide fluid communication between an outer surface of the collar and the inner flow path, one or more valve holes intersecting the fracture ports, one or more valve vent holes positioned to provide fluid communication between the valve holes and the inner flow path, and one or more valves positioned in the valve holes for opening and closing the fracture ports. The valves are configured to open when a pressure differential is created between the fracture ports and the valve vent holes.

The valve holes may comprise an annular area within the collar and the valve may comprise a sleeve movable within the annulus. The annulus may encompass the perimeter of a tubular body of the collar. The sleeve may be movable within the annulus between an open position and a closed position and may further comprise a collet finger adapted to selectively engage a recess on a tubular body of the collar. The collet finger may be configured to selectively retain the sleeve in the open position and/or in the closed position.

The wellbore completion may include a plurality of centralizers extending out from the tubular body. The fracture ports may extend through the plurality of centralizers. The valve holes that intersect the fracture ports may be positioned longitudinally in the centralizers. The valve hole may be an annulus within the collar that intersects the fracture ports. The wellbore completion may further contain a bottom hole assembly positioned in the casing assembly. The bottom hole assembly may include a packer positioned between the fracture ports and the valve vent holes of the collar. The bottom hole assembly may include a straddle packer that may be set in one position to open the valve and set in another position to close the valve.

One embodiment of the present disclosure is a collar configured to connect wellbore casing lengths that includes a mandrel having an inner flow path, an exterior surface, at least one inner fracture port, and at least one valve vent hole. The collar further comprises a housing connected to the exterior surface of the mandrel. The valve housing includes at least one outer fracture port through the housing. A valve is positioned within an annulus between the mandrel and the housing. The housing may be comprised of a valve housing sealingly connected to a vent housing to form an upper and lower portion of the annulus. The annulus is configured to permit fluid communication between the inner fracture port and the outer fracture port. The valve vent hole in the mandrel is configured to permit fluid communication between the inner flow path of the mandrel and the annulus. The valve is movable between an open position that permits fluid communication between the inner and outer fracture ports and a closed position that prevents fluid communication between the inner and outer fracture ports.

The valve may be configured to move between the open and closed positions upon the application of a pressure differential between the fracture ports and the valve vent hole. The valve may be a sleeve that encircles the perimeter of the mandrel. The housing may include a fill port adapted for the injection of grease into the annulus. In the instance the housing is a composite of a valve housing and vent housing, the valve housing and the vent housing may each include a fill port adapted for the injection of grease into the annulus. The injection of grease into the annulus may prevent the ingress of cement into the annulus during the process of cementing the collar into a wellbore. The mandrel may include a burstable device positioned within the valve vent hole to selectively prevent fluid communication between the inner flow path and the annulus. The mandrel may include a plurality of valve vent holes with one of the valve vent holes having a reduced diameter compared to the rest. The reduced diameter may be $\frac{1}{8}^{th}$ inch and the reduced diameter may prevent the ingress of cement into the annulus. The mandrel may further include at least one secondary valve vent hole located uphole from the primary valve vent holes.

One embodiment of the present disclosure is a method for completing a hydrocarbon producing wellbore that includes applying a pressure differential to open a first fracture port of a casing assembly. The casing assembly includes a plurality of casing lengths and one or more collars positioned so as to couple together the casing lengths. A first collar includes a plurality of apertures with one of the apertures being a first fracture port configured to open and close by applying a pressure differential between two apertures on the first collar. For example, the pressure differential may be applied to the first fracture port and at least one other aperture on the first collar. The pressure differential could also be applied to an aperture located uphole of the fracture port and a different aperture located downhole of the fracture port, such as the valve vent hole. The method further comprises fracturing the well formation by flowing fracturing fluid through the first fracture port. The method may also include positioning the casing assembly in the wellhole.

The method may further comprise applying a pressure differential to open a second fracture port on a second collar having a plurality of apertures. One of the apertures on the second collar is the second fracture port configured to open and close by applying a pressure differential between the two apertures on the second collar. The method may further include fracturing a well formation by flowing fracturing fluid through the second fracture port.

The method may further include applying a pressure differential that exceeds the pressure required to fracture the well formation. The method may further include running coiled tubing into the wellhole prior to fracturing and subsequently fracturing while the coiled tubing is in the wellhole. A bottom hole assembly may be attached to the coiled tubing being positioned proximate to the first fracture port through which the fracturing fluid is pumped. The well may be a multi-zone well. The fracture port may comprise a valve capable of moving between an open position and a closed position such that the valve allows fluid communication through the first fracture port in the open position and prevents fluid communication through the first fracture port when in the closed position. The fracture port may be in the closed position while running the coiled tubing into the wellhole. A first collar may be positioned in a first zone of the wellhole and a second collar may be positioned in a second zone of the wellhole. Fracturing of the first zone may comprise moving a valve of the first collar from a closed position to an open position and then fracturing the first zone. Generally, the valves are in the closed position until it is time to begin a fracturing operation. After fracturing the first zone, the method may further include moving a valve of the second collar from a closed position to an open position, isolating the first zone and then fracturing the second zone. This process can be repeated to treat as many zones as required in a single trip of the coiled tubing. The method may include applying a pressure differential between two apertures to close the fracture port after the wellhole is completed.

In one embodiment, the differential pressure at which the valve is opened can be set higher than the pressure required to initiate a fracture in the reservoir. In this way energy can be stored in the fluid contained in the well. The stored energy in the fluid can be used to improve the fracture treatment, as the energy in the fluid can be applied to the reservoir in a shorter period of time as compared to the power available from the pumps through the completion.

One embodiment is a system for use in fracturing a well formation that comprises a first casing segment having an inner flow path and a plurality of centralizers. The centralizers are configured to substantially center the first casing segment within the wellbore with at least one of the centralizers being adjacent a first zone within the well formation. A first fracture port may extend through the centralizer adjacent to the first zone. The first fracture port is adapted to permit fluid communication between the inner flow path of the first casing segment to the first zone.

The first casing segment may include a valve configured to selectively open and close the first fracture port upon the application of a pressure differential. The system may include a second casing segment also having an inner flow path and a plurality of centralizers configured to substantially center the second casing segment within the wellbore. At least one centralizer may include a second fracture port extending through the centralizer and the centralizer may be located adjacent a second zone within the well formation. The second fracture port may be adapted to permit fluid communication between the inner flow path of the second casing segment and the second zone. The second casing segment may include a valve configured to selectively open and close the second fracture port upon the application of a pressure differential. A burstable device may be positioned within the first and/or second fracture ports to selectively prevent fluid communication into the fracture ports.

BRIEF DESCRIPTION OF THE DRAWINGS

FIG. 1 illustrates a portion of a cemented wellbore completion, according to an embodiment of the present disclosure.

FIG. 2 illustrates a close up view of a collar and bottom hole assembly used in the wellbore completion of FIG. 1, according to an embodiment of the present disclosure.

FIG. 3 illustrates a close up view of a locking dog used in the wellbore completion of FIG. 1, according to an embodiment of the present disclosure.

Figure 4:
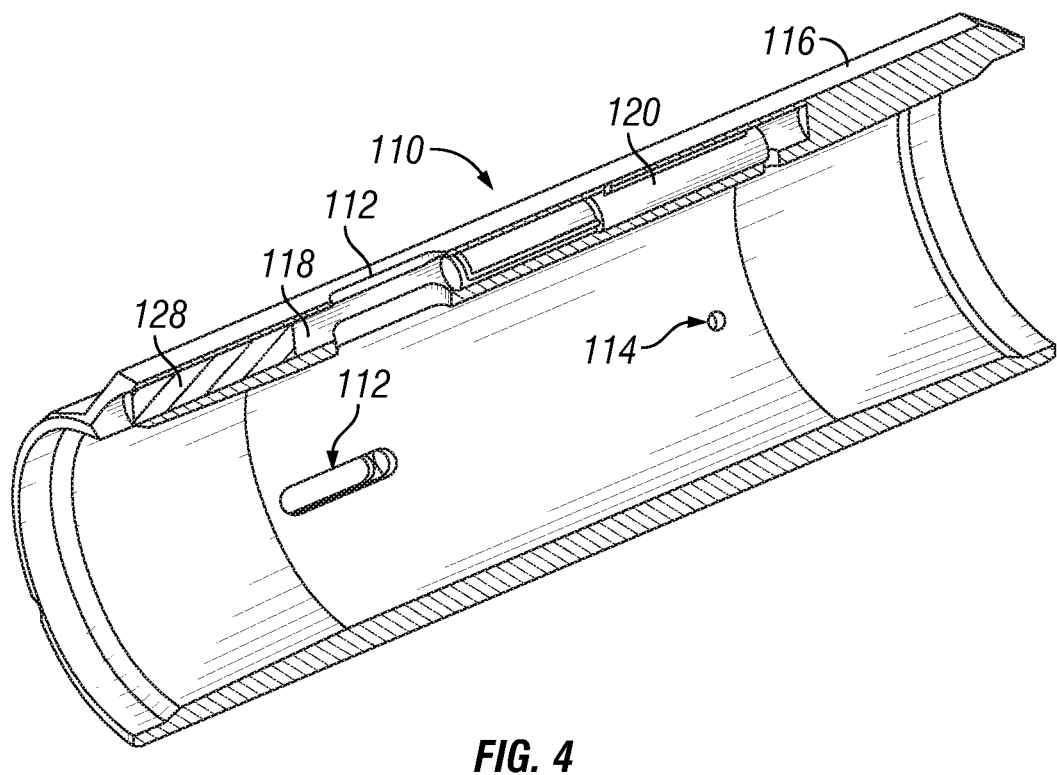
FIG. 4 illustrates a perspective view of a collar, according to an embodiment of the present disclosure.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

FIG. 1 illustrates a portion of a wellbore completion 100, according to an embodiment of the present disclosure. Wellbore completion 100 includes a bottom hole assembly ("BHA") 102 inside a casing 104. Any suitable BHA can be employed. In an embodiment, the BHA 102 can be designed for carrying out fracturing in a multi-zone well. An example of a suitable BHA is disclosed in copending U.S. patent application Ser. No. 12/626,006, filed Nov. 25, 2009, in the name of John Edward Ravensbergen and entitled, COILED TUBING BOTTOM HOLE ASSEMBLY WITH PACKER AND ANCHOR ASSEMBLY, the disclosure of which is hereby incorporated by reference in its entirety.

As more clearly illustrated in FIGS. 2 and 3, casing 104 can include multiple casing lengths 106A, 106B and 106C that can be connected by one or more collars, such as collars 108 and 110. Casing lengths 106A, 106B, and/or 106C may be pup joints, segments of casing approximately six (6) feet in length, which may be configured to aid in properly locating a BHA within a desired zone of the wellbore. Collar 108 can be any suitable collar. Examples of collars for connecting casing lengths are well known in the art. In an embodiment, collar 108 can include two female threaded portions for connecting to threaded male ends of the casing lengths 106.

A perspective view of collar 110 is illustrated in FIG. 4, according to an embodiment of the present disclosure. Collar 110 can include one or more fracture ports 112 and one or more valve vent holes 114. Fracture ports 112 can intersect valve holes 118, which can be positioned longitudinally in centralizers 116. A plug 128 can be positioned in valve holes 118 to prevent or reduce undesired fluid flow up through valve holes 118. In an embodiment, the inner diameter 113 (shown in FIG. 2) of the collar 110 can be approximately the same or greater than the inner diameter of the casing 104. In this way, the annulus between the collar 110 and the BHA 102 is not significantly restricted. In other embodiments, the inner diameter of the collar 110 can be less than the inner diameter of the casing 104. Collar 110 can attach to casing lengths 106 by any suitable mechanism. In an embodiment, collar 110 can include two female threaded portions for connecting to threaded male ends of the casing lengths 106B and 106C.

Figure 5:
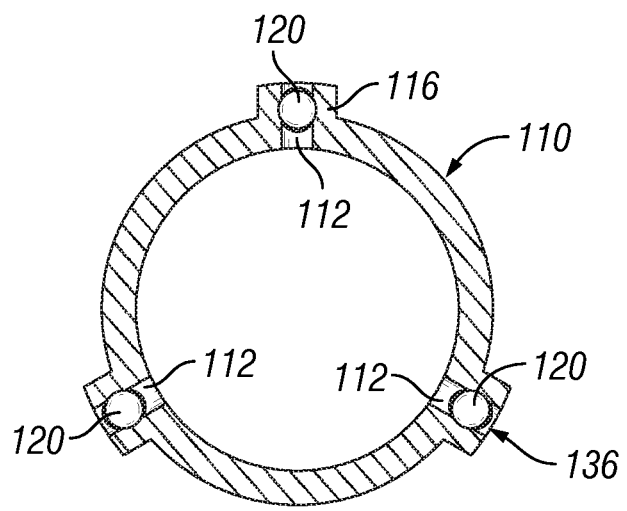
FIG. 5 illustrates a cross-sectional view of the collar of FIG. 4, according to an embodiment of the present disclosure.

As more clearly shown in FIG. 5, fracture ports 112 can be positioned through centralizers 116, which can allow the fracture port 112 to be positioned relatively close to the formation. Where the casing is to be cemented into the wellbore, this can increase the chance that the fracture ports 112 will reach through, or nearly through, the cement.

Figure 6:
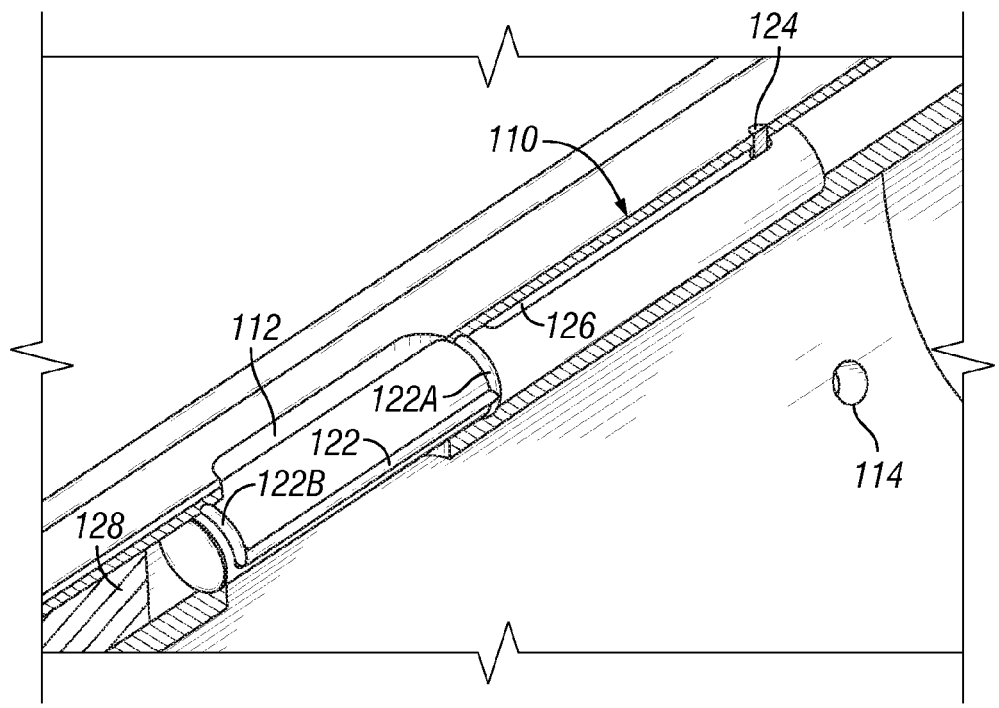
FIG. 6 illustrates a valve used in the collar of FIG. 4, according to an embodiment of the present disclosure.

Valves 120 for controlling fluid flow through fracture ports 112 are positioned in the valve holes 118 of centralizers 116. When the valves 120 are in the closed position, as illustrated in FIG. 6, they prevent or reduce the flow of fluid through the fracture ports 112.

Valves 120 can include one or more seals to reduce leakage. Any suitable seal can be employed. An example of a suitable seal 122 is illustrated in FIG. 6. Seal 122 can be configured to extend around the fracture port 112 when valve 120 is positioned in the closed position. Seal 122 can include a ring 122A that fits around the circumference of valve 120 at one end and a circular portion 122B that extends only around a portion of the valve 120 at the opposite end. This configuration can provide the desired sealing effect while being easy to manufacture.

A shear pin 124 can be used to hold the valve 120 in the closed position during installation and reduce the likelihood of valve 120 opening prematurely. Shear pin 124 can be designed so that when it is sheared, a portion of the pin 124 remains in the wall of collar 110 and extends into groove 126 of valve 120. This allows the sheared portion of pin 124 to act as a guide by maintaining the valve 120 in a desired orientation so that seal 122 is positioned correctly in relation to fracture port 112. The use of sheared pin 124 as a guide is illustrated in FIG. 2, which shows the valve 120 in open position.

Collar 110 can be attached to the casing lengths in any suitable manner. In an embodiment, collar 110 can include two female threaded portions for connecting to threaded male ends of the casing lengths 106, as illustrated in FIG. 2.

As also shown in FIG. 2, a packer 130 can be positioned in the casing between the fracture ports 112 and the valve vent hole 114. When the packer 130 is energized, it seals on the inner diameter of the collar 110 to prevent or reduce fluid flow further down the well bore annulus. Thus, when fluid flows downhole from surface in an annulus between a well casing 104 and a BHA 102, a pressure differential is formed across the packer between the fracture port 112 and the valve vent hole 114. The pressure differential can be used to open the valve 120.

Any suitable technique can be employed to position the packer 130 at the desired position in the collar 110. One example technique illustrated in FIG. 3 employs a dog 132 that can be configured so as to drive into a recess 134 between casing portions 106A and 106B. As shown in FIG. 1, the dog 132 can be included as part of the BHA 102. The length of the casing portion 106B can then be chosen to position the collar 110 a desired distance from the recess 134 so that the packer 130 can be positioned between the fracture port 112 and the valve vent hole 114. During installation, the well operator can install the BHA 102 by lowering the dog past the recess 134 and then raising the BHA 102 up until the dog 132 drives into the recess 134. An extra resistance in pulling dog 132 out of the recess 134 will be detectable at the surface and can allow the well operator to determine when the BHA 102 is correctly positioned in the casing. This can allow the well operator to locate the packer 130 relative to the standard collar 108, which can be the next lowest collar relative to collar 110.

Figure 8:
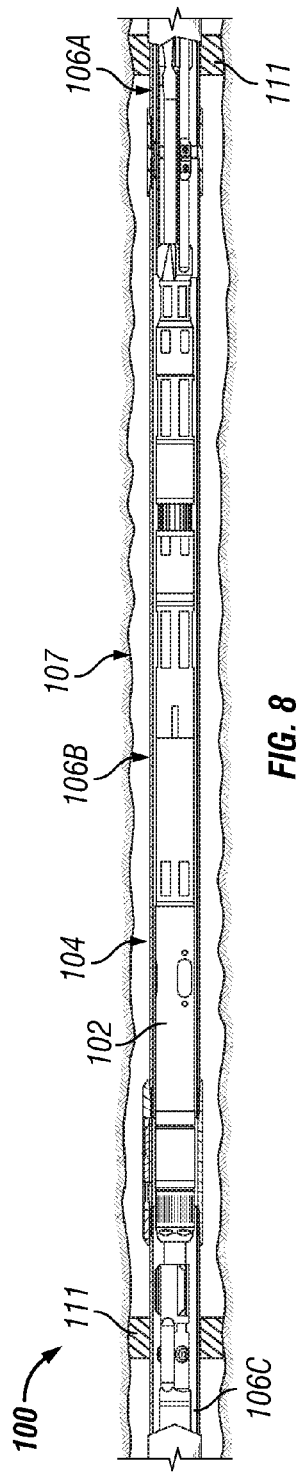
FIG. 8 illustrates a portion of a well completion with openhole packers, according to an embodiment of the present disclosure.

The casing 104 can be installed after well drilling as part of the completion 100. In an embodiment, the casing 104, including one or more collars 110, can be cemented into the wellbore. FIG. 1 illustrates the cement 105, which is flowed into the space between the outer diameter of the casing 104 and the inner diameter of the wellhole 107. Techniques for cementing in casing are well known in the art. In another embodiment, the casing 104 and collars 110 can be installed in the wellbore using an open hole packer arrangement where instead of cement, packers 111 are positioned between the inner diameter of the wellbore 107 and the outer diameter of the casing 104, as illustrated in FIG. 8. Such open hole packer completions are well known in the art and one of ordinary skill in the art would readily be able to apply the collars of the present application in an open hole packer type completion.

The collars 110 can be positioned in the casing wherever ports are desired for fracturing. For example, it is noted that while a standard collar 108 is shown as part of the casing, collar 108 can be replaced by a second collar 110. In an embodiment, the collars 110 of the present disclosure can be positioned in each zone of a multi-zone well.

During the cementing process, the casing is run in and cement fills the annular space between casing 104 and the well formation. Where the valve 120 is positioned in the centralizer, there can be a slight depression 136 between the outer diameter of the centralizer 116 and the outer diameter of valve 120, as shown in FIG. 5. The depression 136 can potentially be filled with cement during the cementing process. Therefore, before fluid flows through the valve 120, there may be a thin layer of cement that will have to be punched through. Alternatively, the depression 136 may not be filled with cement. In an embodiment, it may be possible to fill the depression 136 with grease, cement inhibiting grease, or other substance prior to cementing so as to reduce the likelihood of the depression 136 being filled with cement.

A potential advantage of the collar design of FIG. 4 is that opening valve 120 displaces fluid volume from the valve hole 118 into an annulus between the casing 106 and the BHA 102 through the valve vent hole 114. Thus, all of the displaced volume that occurs when opening the valves 120 is internal to the completion. This allows filling the space between the wellbore and the outer diameter of casing 106 with cement, for example, without having to necessarily provide a space external to the collar for the fluid volume that is displaced when valve 120 is opened.

Another possible advantage of the collar design of FIG. 4 is that little or no pressure differential is likely to be realized between the fracture port 112 and the valve vent hole 114 of a collar 110 until the inner diameter of the collar is sealed off between the fracture port 112 and the valve vent hole 114. This means that in multi-zone wells having multiple collars 110, the operator can control which fracture port is opened by position the sealing mechanism, such as the packer 130, in a desired location without fear that other fracture ports at other locations in the well will inadvertently be opened.

The collars of the present disclosure can be employed in any type of well. Examples of well types in which the collars can be used include horizontal wells, vertical wells and deviated wells.

The completion assemblies shown above with respect to FIGS. 1 to 3 are for annular fracturing techniques where the fracturing fluid is pumped down a well bore annulus between a well casing 104 and a BHA 102. However, the collars 110 of the present disclosure can also be employed in other types of fracturing techniques.

Figure 7:
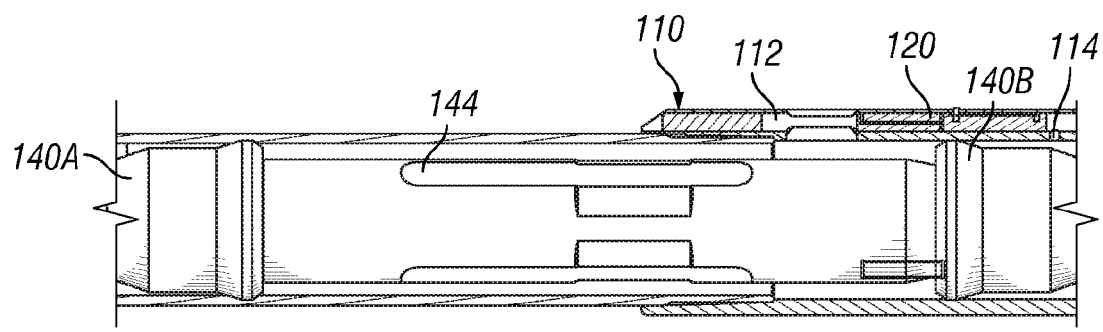
FIG. 7 illustrates a collar being used with a coiled tubing string and a straddle tool having packers for isolating a zone in the well to be fractured, according to an embodiment of the present disclosure.

One such fracturing technique is illustrated in FIG. 7, where a coiled tubing string is employed with a straddle tool having packers 140A, 140B for isolating a zone in the well to be fractured. As shown in FIG. 7, the packer 140B can be positioned between the fracture port 112 and the valve vent hole 114. This allows valve 120 to be opened by creating a pressure differential between fracture port 112 and valve vent hole 114 when the area in the wellbore between packers 140A, 140B is pressured up. Pressuring up can be accomplished by flowing a fluid down the coiled tubing at a suitable pressure for opening the valve 120. The fluid for opening valve 120 can be a fracturing fluid or another suitable fluid. After the valve 120 is opened, fracturing fluid (not shown) can be pumped downhole through coiled tubing, into the annulus through aperture 144 and then into the formation through fracture port 112. A potential advantage of the coiled tubing/straddle tool assembly of FIG. 7 is that any proppant used during the fracturing step can be isolated between the packers 140A and 140B from the rest of the wellbore annulus.

A method for multi-zone fracturing using the collars 110 of the present disclosure will now be described. The method can include running the casing 104 and collars 110 into the wellhole after drilling. The casing 104 and collars 110 can be either set in the wellhole by cementing or by using packers in an openhole packer type assembly, as discussed above. After the casing is set in the wellhole, a BHA 102 attached to the end of coiled tubing string can be run into the well. In an embodiment, the BHA 102 can initially be run to, or near, the bottom of the well. During the running in process, the dogs 132 (FIG. 3) are profiled such that they do not completely engage and/or easily slide past the recesses 134. For example, the dogs 132 can be configured with a shallow angle 131 on the down hole side to allow them to more easily slide past the recess 134 with a small axial force when running into the well.

After the BHA 102 is run to the desired depth, the well operator can start pulling the tubing string and BHA 102 up towards the surface. Dogs 132 can be profiled to engage the recess 134 with a steep angle 133 on the top of the dogs 132, thereby resulting in an increased axial force in the upward pull when attempting to pull the dogs 132 out of the recesses. This increased resistance allows the well operator to determine the appropriate location in the well to set the packer 130, as discussed above. Profiling the dogs 132 to provide a reduced resistance running into the well and an increased resistance running out of the well is generally well known in the industry. After the packer 130 is positioned in the desired location, the packer 130 can then be activated to seal off the well annulus between the BHA 102 and the desired collar 110 between the fracture port 112 and the valve vent hole 114.

After the well annulus is sealed at the desired collar 110, the well annulus can be pressured up from the surface to a pressure sufficient to open the valves 120. Suitable pressures can range, for example, from about 100 psi to about 10,000 psi, such as about 500 psi to about 1000 psi, 1500 psi or more. The collar 110 is designed so that all of the fracture ports 112 in the collar may open. In an embodiment, the pressure to open the fracture ports 112 can be set lower than the fracturing pressure. This can allow the fracturing pressure, and therefore the fracturing process itself, to ensure all the fracture ports 112 are opened. It is contemplated, however, that in some situations all of the fracture ports 112 may not be opened. This can occur due to, for example, a malfunction or the fracture ports being blocked by cement. After the fracture ports 112 are opened, fluids can be pumped through the fracture ports 112 to the well formation. The fracture process can be initiated and fracturing fluids can be pumped down the well bore to fracture the formation. Depending on the fracturing technique used, this can include flowing fracturing fluids down the well bore annulus, such as in the embodiment of FIGS. 1 to 3. Alternatively, fracturing fluids can be flowed down a string of coiled tubing, as in the embodiment of FIG. 7. If desired, a proppant, such as a sand slurry, can be used in the process. The proppant can fill the fractures and keep them open after fracturing stops. The fracture treatment typically ends once the final volume of proppant reaches the formation. A displacement fluid is used to push the proppant down the well bore to the formation.

A pad fluid is the fluid that is pumped before the proppant is pumped into the formation. It ensures that there is enough fracture width before the proppant reaches the formation. If ported collar assemblies are used, it is possible for the displacement fluid to be the pad fluid for the subsequent treatment. As a result, fluid consumption is reduced.

In multi-zone wells, the above fracturing process can be repeated for each zone of the well. Thus, the BHA 102 can be set in the next collar 110, the packer can be energized, the fracturing port 112 opened and the fracturing process carried out. The process can be repeated for each zone from the bottom of the wellbore up. After fracturing, oil can flow out the fracture through the fracture ports 112 of the collars 110 and into the well.

In an alternative multi-zone embodiment, the fracturing can potentially occur from the top down, or in any order. For example, a straddle tool, such as that disclosed in FIG. 7, can be used to isolate the zones above and below in the well by techniques well known in the art. The fracture ports 112 can then be opened by pressuring up through the coiled tubing, similarly as discussed above. Fracturing can then occur for the first zone, also in a similar fashion as described above. The straddle tool can then be moved to the second zone form the surface and the process repeated. Because the straddle tool can isolate a collar from the collars above and below, the straddle tool permits the fracture of any zone along the wellbore and eliminates the requirement to begin fracturing at the lower most zone and working up the casing.

The design of the collar 110 of the present disclosure can potentially allow for closing the valve 120 after it has been opened. This may be beneficial in cases were certain zones in a multi-zone well begin producing water, or other unwanted fluids. If the zones that produce the water can be located, the collars associated with that zone can be closed to prevent the undesired fluid flow from the zone. This can be accomplished by isolating the valve vent hole 114 and then pressuring up to force the valve 120 closed. For example, a straddle tool can be employed similar to the embodiment of FIG. 7, except that the packer 140A can be positioned between the fracture port 112 and the valve vent hole 114, and the lower packer 140B can be positioned on the far side of the valve vent hole 114 from packer 140A. When the zone between the packers is pressurized, it creates a high pressure at the valve vent hole 114 that forces the valve 120 closed.

Erosion of the fracture port 112 by the fracturing and other fluids can potentially prevent the valve 120 from sealing effectively to prevent fluid flow even through the fracture port 112 is closed. However, it is possible that the design of the collar 110 of the present disclosure, which allows multiple fracture ports in a single collar to open, may help to reduce erosion as compared to a design in which only a single fracture port were opened. This is because the multiple fracture ports can provide a relatively large flow area, which thereby effectively decreases the pressure differential of the fluids across the fracture port during fracturing. The decreased pressure differential may result in a desired reduction in erosion.

Figure 10:
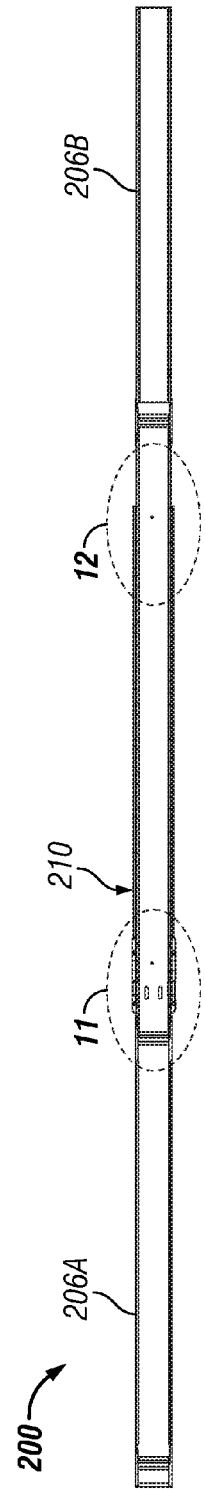
FIG. 10 illustrates a bottom hole assembly used in a wellbore completion, according to an embodiment of the present disclosure.
Figure 11:
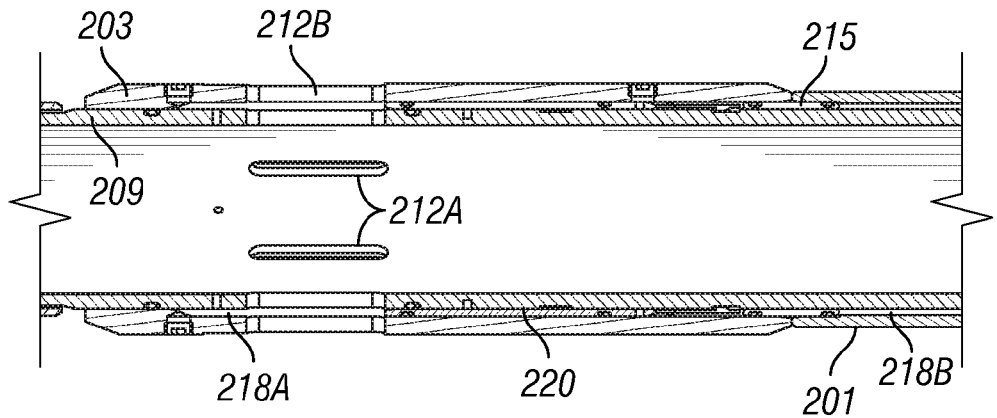
FIG. 11 illustrates a close up view of the upper portion of a collar and bottom hole assembly embodiment shown in FIG. 10.
Figure 12:
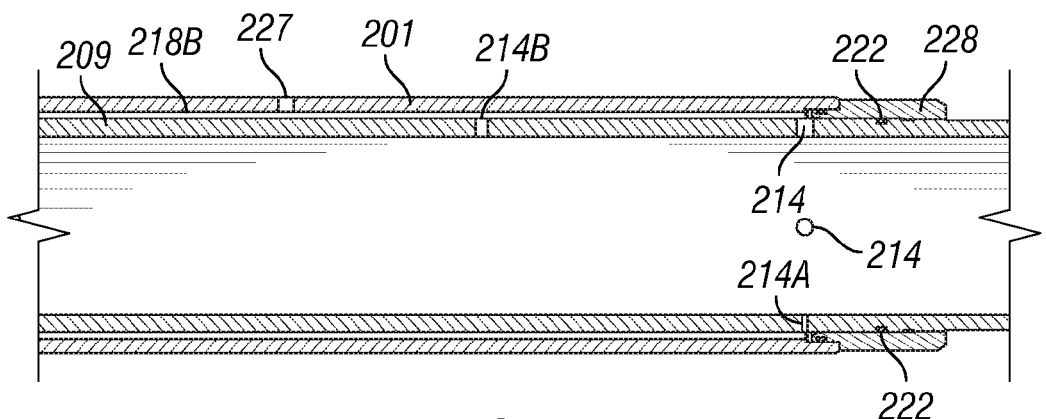
FIG. 12 illustrates a close up view of a lower portion of the collar and bottom hole assembly embodiment shown in FIG. 10.

FIG. 10 illustrates a portion of a wellbore completion 200, according to an embodiment of the present disclosure. The wellbore completion includes casing lengths 206a, 206b connected to a collar assembly 210, herein after referred to as collar 210. FIG. 11 shows a close-up view of the upper portion of the collar 210 and FIG. 12 shows a close-up view of the lower portion of the collar 210. The collar 210 shown in FIG. 11 comprises a mandrel 209, which may comprise a length of casing length, a valve housing 203, and a vent housing 201. A valve, such as a sleeve 220, is positioned within an annulus 218 between the mandrel 209 and the valve housing 203. The sleeve 220 is movable between an open position (shown in FIG. 10) that permits communication between the inner diameter of the mandrel 209 and outer fracture ports 212B through inner fracture port 212A located in the mandrel 209. The annulus 218A extends around the perimeter of the mandrel and is in communication with the annulus 218B between the vent housing 201 and the mandrel 209, which may be referred to as a single annulus 218. The sleeve 220 may be moved into a closed position (shown in FIG. 15) preventing fluid communication between the inner fracture port 212A and outer fracture port 212B, which may be referred to collectively as the fracture port 212. The sleeve 220 effectively seals the annulus 218 into an upper portion 218A and 218B thus, permitting a pressure differential between the two annuluses to move the sleeve 220 between its open and closed positions. A seal ring 215 may be used connect the valve housing 203 to the vent housing 201. Grooves 218C in the mandrel under the seal ring ensure good fluid communication past the seal ring 215 between the upper portion 218A and lower portion 218B of the annulus 218. Alternatively, the valve housing and the vent housing may be a single housing. In this embodiment, a seal ring to connect the two housings and grooves in the mandrel to provide fluid communication would not be necessary.

FIG. 12 shows that the lower portion of the vent housing 201 and the mandrel 209 having an annulus 218B between the two components. A lower nut 228 connects the lower end of the vent housing 201 to the mandrel 209 with sealing elements 222 sealing off the lower portion of the annulus 218B. The mandrel 209 includes a vent hole 214 that is in communication with the annulus 218. In one embodiment, a plurality of vent holes 214 are positioned around the mandrel 209. The mandrel may include one or more vent holes 214B at a different location the primary vent holes 214. In operation a burstable device, such as a burst plug, or cement inhibiting grease may fill each of the vent holes to prevent cement, or other undesired substances, from entering into the annulus 218. In addition to the burst plugs, cement inhibiting grease may be injected into the annulus 218 prior to the completion being run into the wellbore to prevent the ingress of cement into the annulus 218 while the completion is cemented into a wellbore. The vent housing 201 may include a fill port 227 to aid in the injection of grease into the annulus 218. Preferably, one of the vent holes may be significantly smaller in diameter than the rest of the vent holes and not include a burst plug. After bursting the burst plugs, the vent holes permit the application of pressure differential in the annulus 218 to open or close the valve 220, as detailed above. In the event that the cement has entered into the annulus 218 via the vent holes 214, the vent housing may include secondary vent hole(s) 214B farther uphole along the mandrel 209 that may permit communication to the annulus 218.

Figure 13:
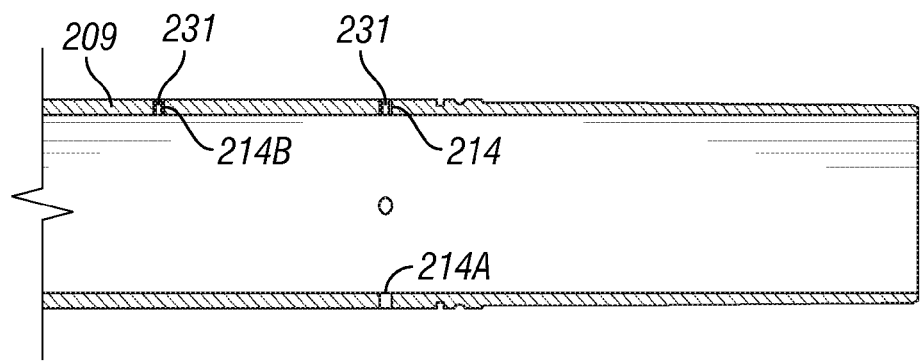
FIG. 13 illustrates close up view of a portion of a mandrel of a bottom hole assembly, according to an embodiment of the present disclosure.

FIG. 13 illustrates the downhole portion of the mandrel 209 without the vent housing 201. Burst plugs 231 have been inserted into vent holes 214, 214B. Preferably, a burst plug is not inserted into the smallest vent hole 214A, which may be approximately ⅛ inch in diameter. The vent housing 201 is adapted to provide predetermined distance between the fracture ports 212 and the vent hole(s) 214. The vent holes 214 may be approximately two (2) meters from the fracture ports to provide adequate spacing for the location of a packing element to permit the application of a pressure differential. It is difficult to position the packing element accurately, within half of a meter, in the well bore. In addition, the position of the collars relative to each other is often not accurately known, largely due to errors in measurements taken when the completion is installed into the well bore. The challenge to accurately position the packing element within the well bore is due to several factors. One factor is the equipment used to measure the force exerted on the coiled tubing while pulling out of the hole is not exact, often errors of 1000 lbs. force or more can occur. The casing collar locating profile (133) of FIG. 1 typically increases the force to pull out of the hole by 2000 lbs. In addition, the frictional force between the coiled tubing and the casing in a horizontal well is high and not constant, while pulling out of the well. As a result it can be difficult to know what is causing an increase in force observed at the surface. It could be due to the casing collar locator pulling into a coupling or it could be due to other forces between the coiled tubing and the completion and/or proppant. A strategy used to improve the likelihood of determining the position of the packing element is to use short lengths of casing, typically two (2) meters long, above and below the collar assembly. In this way there are three or four couplings (dependent on the configuration of the collar) at known spacing distinct from the standard length of casing, which are typically thirteen (13) meters long. As a result of using short lengths of casing attached directly to the collar assembly, absolute depth measurement relative to the surface or relative to a recorded tally sheet are no longer required. However, this distance between the fracture port and the vent hole may be varied to accommodate various packing elements or configurations to permit the application of a pressure differential as would be appreciated by one of ordinary skill in the art having the benefit of this disclosure.

Figure 9:
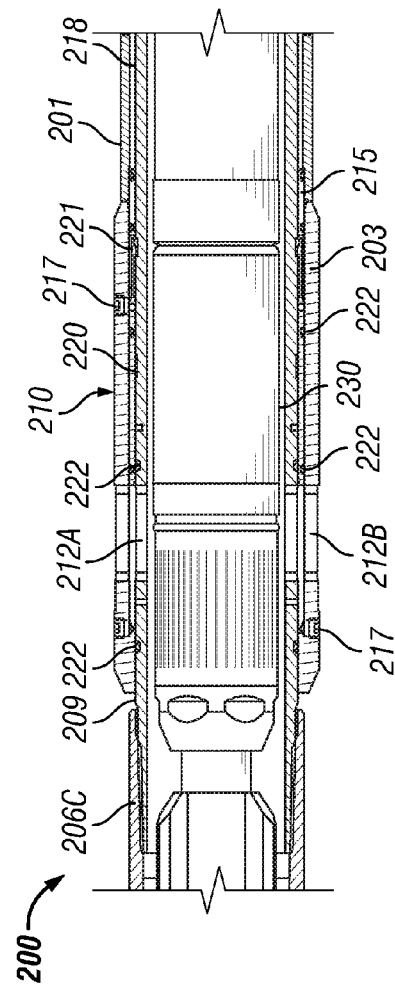
FIG. 9 illustrates a close up view of a collar and bottom hole assembly, according to an embodiment of the present disclosure.

FIG. 9 illustrates a portion of a wellbore completion 200, according to an embodiment of the present disclosure that includes a BHA inside of a casing made up of a plurality of casing lengths 206 connected together via a plurality of collars, such as collar 210. The collar 210 in this embodiment is comprised of a mandrel 209, a valve housing 203, and a vent housing 201. A valve, such as a sleeve 220, is positioned within an annulus 218 between the mandrel 209 and the valve housing 203. The sleeve 220 is movable between an open position (shown in FIG. 9) that permits communication between the inner diameter of the mandrel 209 and the outer fracture ports 212B via the inner fracture ports 212A. The sleeve 220 includes a collet finger 221 that is configured to engage a recess 223 (shown on FIG. 15) on the mandrel 209 to selectively retain the sleeve 220 in its open position. Sealing elements 222 may be used to provide seal between the valve housing 203, the mandrel 209, and the sleeve 220. The valve housing 203 may include one or more fill ports 217 that permits the injection of grease or other cement inhibiting substances into the annulus 218 to prevent the ingress of cement if the completion 200 is cemented into the wellbore.

Figure 15:
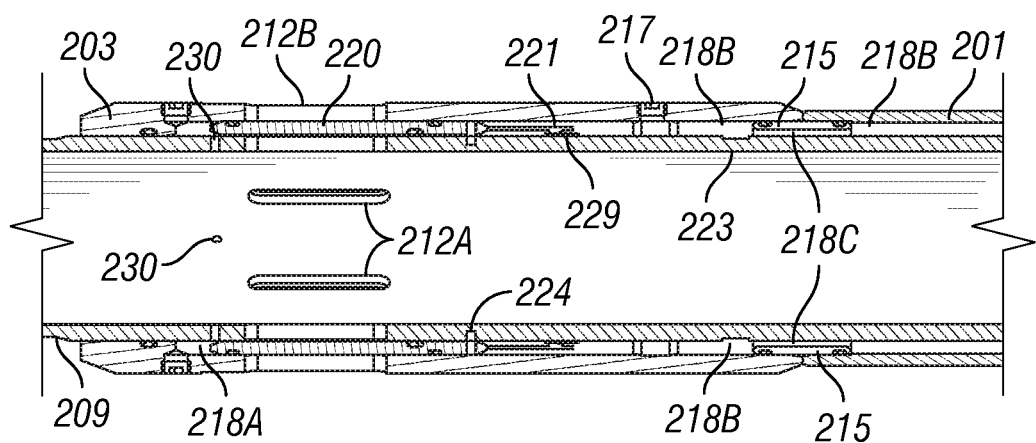
FIG. 15 illustrates a cross-section view of a collar having a valve in the closed position, according to an embodiment of the present disclosure.

FIG. 15 shows a cross-section view of the upper portion of the collar 210 with the sleeve 220 in a closed position. A shear pin 224 selectively retains the sleeve 220 in the closed position. The shear pin 224 can be used to hold the sleeve 220 in the closed position during installation and reduce the likelihood of sleeve 220 (or valve 120) opening prematurely. The shear pin 224 may be adapted to shear and release the sleeve 220 upon the application of a predetermined pressure differential as would be appreciated by one of ordinary skill in the art. The mandrel 209 may include one or more ports 230 that are positioned uphole of the closed sleeve 220 to aid in the application of a pressure differential into the annulus 218A above the sleeve 220 when moving the sleeve 220 to the open position. After opening the sleeve and fracturing the wellbore, the sleeve 220 may be moved back to the closed position upon the application of a pressure differential as discussed above. The ports 230 in the mandrel 209 may permit the exit of fluid from the annulus 218A as the sleeve 220 passes the fracture ports 212 as it moves to the closed position. The mandrel 209 may include a recess 229 adapted to mate with the collet finger 221 and selectively retain the sleeve 220 in the closed position until the application of another pressure differential. In the shown embodiment, the sleeve 220 encompasses the entire perimeter of the mandrel 209. Alternatively, a plurality of sleeves may be used to selectively permit fluid communication with the fracture ports 212.

Figure 14:
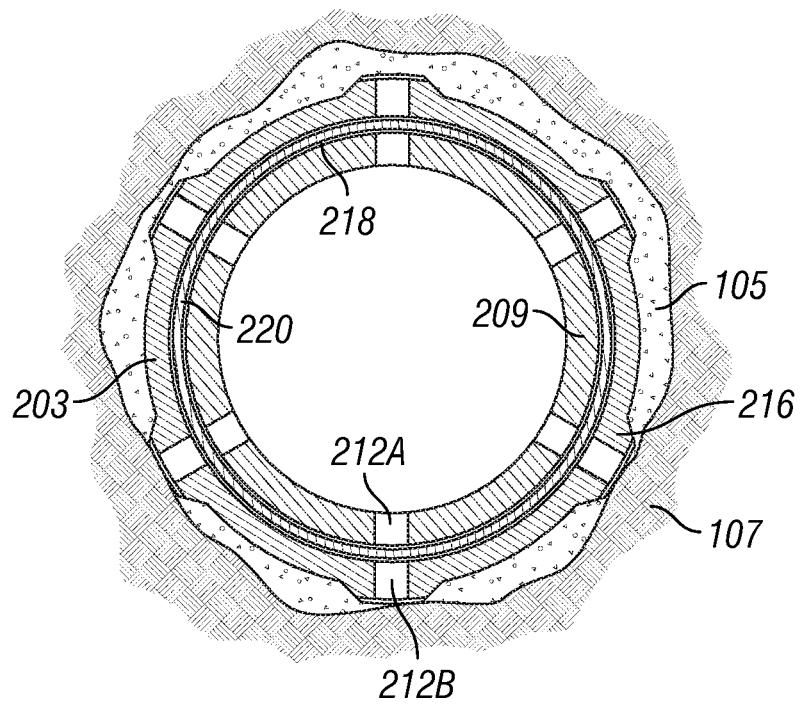
FIG. 14 illustrates a cross-sectional end view of the collar of FIG. 11.

The collar 210 can include one or more inner fracture ports 212A, one or more outer fracture ports 212B, and one or more valve vent holes 214 (shown in FIG. 12). The outer fracture ports 212B intersect the annulus 218 and may be positioned in centralizers 216 along the outside of the collar 210 (as shown in FIG. 14). In an embodiment, the inner diameter of the collar 210 can be approximately the same or greater than the inner diameter of the casing. In this way, the annulus between the collar 210 and the BHA is not significantly restricted. One potential challenge of this process is the reliable use of a packer that is typically used within casings that potentially have a large variation in the inner diameter between the segments of casing. The use of ported collars 210 may decrease this potential problem because the ported collars 210 can be made with a smaller variation in the inner diameter as well as having a less oval shape than typical casing. These improvements provide improved reliability for properly sealing off within the collars 210 with a typical packer. In other embodiments, the inner diameter of the collar 210 can be less than the inner diameter of the casing. However, the inner diameter of the collar 210 may still be within tolerance limits of the inner diameter of the casing. Collar 210 can attach to casing lengths 106 by any suitable mechanism. In an embodiment, collar 210 can include two female threaded portions for connecting to threaded male ends of the casing lengths 206b and 206c.

As more clearly shown in FIG. 14, the outer fracture ports 212B can be positioned through centralizers 216, which can allow the outer fracture port 212B to be positioned relatively close to the formation 107. Where the casing is to be cemented into the wellbore, this can increase the chance that the fracture ports 112 will reach through, or nearly through, the cement 105. As shown in FIG. 14, one or more of the centralizers 216 may be in direct contact with the open hole formation 107, which may be the centralizers 216 on the lower side in a horizontal well as would be appreciated by one of ordinary skill in the art having the benefit of this disclosure. A valve, such as a sleeve 220, may be positioned in an annulus in fluid communication with both inner fracture ports 212A and outer fracture ports 212B. The annulus 218 may be between the mandrel 209 and an outer valve housing 203. When the sleeve 220 is in the closed position, as illustrated in FIG. 15, it prevents or reduces the flow of fluid through the fracture ports 112.

As shown in FIG. 9, a packer 230 can be positioned in the casing between the fracture ports 212 and the valve vent holes 214. When the packer 230 is energized, it seals on the inner diameter of the collar 210 to prevent or reduce fluid flow further down the well bore annulus. Thus, when fluid flows downhole from surface in the annulus between a well casing 104 and a BHA, a pressure differential is formed across the packer between the fracture ports 212 and the valve vent holes 214. The pressure differential can be used to open the valve 220. The user of the packer in FIG. 9 to create a differential pressure is provided for illustrative purposes as various tools and techniques may be employed to create a differential pressure to open and/or close the valves, as would be appreciated by one of ordinary skill in the art. For example, a rotary jetting tool could potential run into casing and directed to the valve vent holes to create the pressure differential required to close the valve.

As discussed above, during the cementing process the casing is run in and cement is pumped down the central bore of the casing and out of the end of the casing 104 filling the annular space between casing 104 and the well formation. To preventingress of cement and/or fluids used during the cementing process, grease or other substance may be injected into the annulus 218 of the collar 210 prior to running the casing into the wellbore. Burst plugs may be inserted into the valve vent holes 214 and grease may be injected into the annulus through injection ports in the valve housing 203 and the vent housing 201. Afterwards the injection ports may be plugged.

Figure 16:
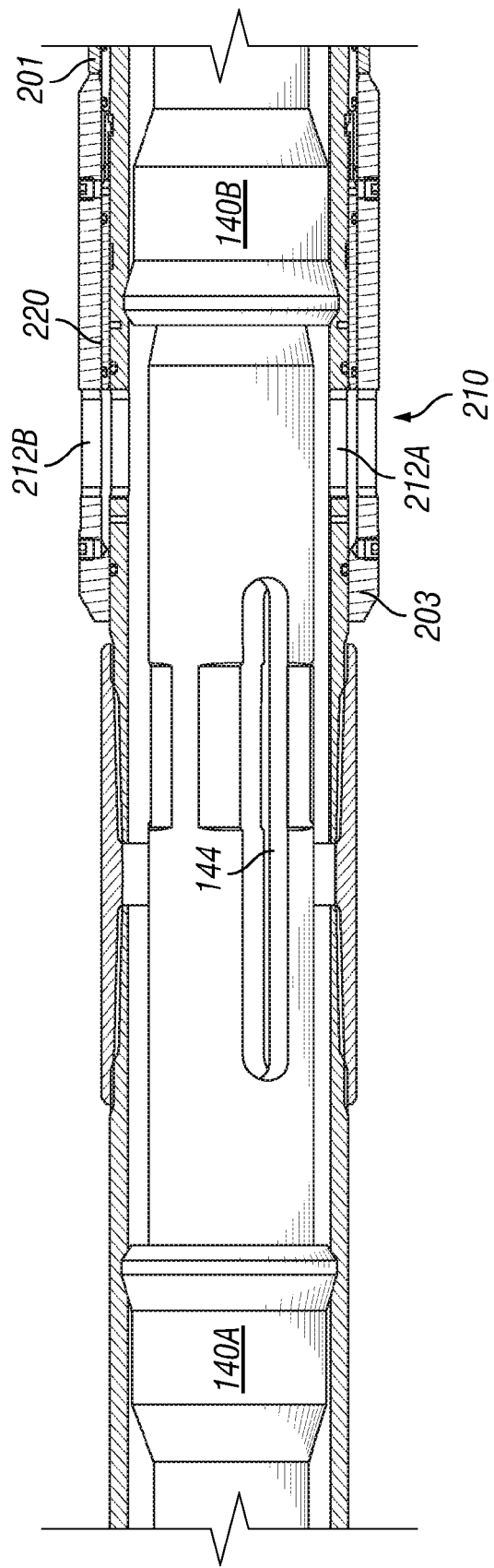
FIG. 16 illustrates a collar being used with a coiled tubing string and a straddle tool having packers for isolating a zone in the well to be fractured, according to an embodiment of the present disclosure.

FIG. 16 shows one technique used to open the sleeve 220 to fracture the formation. A coiled tubing string is employed with a straddle tool having packers 140A,140B for isolating a zone in the well to be fractured. FIG. 16 shows only a portion of the straddle tool that may be used with the collar assembly of the present disclosure. As shown in FIG. 16, the downhole packer 140B can be positioned between the fracture ports 212 and the valve vent holes 214 (shown in FIG. 12). This allows sleeve 220 to be opened by creating a pressure differential between the fracture ports 212 and valve vent holes 214 when the area in the wellbore between packers 140A, 140B is pressured up. Pressuring up can be accomplished by flowing a fluid down the coiled tubing and out of aperture 144 at a suitable pressure for opening the valve 220. The fluid use to open the sleeve 220 may be fracturing fluid. A potential advantage of the coiled tubing/straddle tool assembly of FIG. 16 is that any proppant used during the fracturing step can be isolated between the packers 140A and 140B from the rest of the annulus. In one embodiment the sleeve 220 may be adapted to open at predetermined pressure differential well above the desire fracturing pressure. Thus, energy may be stored within the coiled tubing prior to opening the sleeve 220 and the formation may be fractured very rapidly after opening the fracture ports 212.

A method for multi-zone fracturing using the collars 210 of the present disclosure will now be described. The method can include running the casing 104 and collars 210 into the wellhole after drilling. The casing 104 and collars 210 can be either set in the wellhole by cementing or by using packers in an openhole packer type assembly, as discussed above. After the casing is set in the wellhole, a BHA attached to the end of coiled tubing string or jointed pipe can be run into the well. In an embodiment, the BHA can initially be run to, or near, the bottom of the well. During the running in process, the dogs 132 (FIG. 3) are profiled such that they do not completely engage and/or easily slide past the recesses 134. For example, the dogs 132 can be configured with a shallow angle 131 on the down hole side to allow them to more easily slide past the recess 134 with a small axial force when running into the well.

After the BHA is run to the desired depth, the well operator can start pulling the coiled tubing string and BHA up towards the surface. Dogs 132 can be profiled to engage the recess 134 with a steep angle 133 on the top of the dogs 132, thereby resulting in an increased axial force in the upward pull when attempting to pull the dogs 132 out of the recesses. This increased resistance allows the well operator to determine the appropriate location in the well to set the packer 230, as discussed above. Profiling the dogs 132 to provide a reduced resistance running into the well and an increased resistance running out of the well is generally well known in the industry. After the packer 230 is positioned in the desired location, the packer 230 can then be activated to seal off the well annulus between the BHA and the desired collar 210 between the fracture port 212 and the valve vent hole 214.

After the well annulus is sealed at the desired collar 210, the well annulus can be pressured up from the surface to a pressure sufficient to open the valve 220. Suitable pressures can range, for example, from about 100 psi to about 10,000 psi, such as about 500 psi to about 1000 psi, 1500 psi or more. As discussed above, the suitable pressure may be adapted to exceed the desired fracturing pressure to aid in the rapid fracture of the formation.

After the fracture ports 212 are opened, fluids can be pumped through the fracture ports 212 to the well formation. The fracture process can be initiated and fracturing fluids can be pumped down the well bore to fracture the formation. If desired, a proppant, such as a sand slurry, can be used in the process. The proppant can fill the fractures and keep them open after fracturing stops. After fracturing, the BHA can be used to remove any undesired proppant/fracturing fluid from the wellbore.

In multi-zone wells, the above fracturing process can be repeated for each zone of the well. Thus, the BHA can be set in the next collar 210, the packer can be energized, the fracturing ports 212 opened and the fracturing process carried out. The process can be repeated for each zone from the bottom of the wellbore up. After fracturing, oil can flow out the fracture through the fracture ports 212 of the collars 210 and into the well. When the BHA as shown in FIG. 1 is used, the first treatment may be placed at the bottom of the well and each subsequent treatment may be placed incrementally higher in the well. The fracturing treatments for each zone may be done all in a single trip of the BHA with minimal time required between the fracturing of each zone. The collar assemblies of the present disclosure that are positioned in the zones above the current treatment are exposed to current treatment well bore pressures. This pressure at times may be limited by the pressure rating of the casing. However, there is no risk of the valves of these collar assemblies prematurely opening because the pressure is balanced across the valves. The valves of the present disclosure can only be opened with a pressure differential between the fracture port and the valve vent hole. Further, the present disclosure provides for an efficient use of fluid during the fracturing process as the displacement fluid for a current zone being fractured can act as the pad fluid for the next zone to be treated.

The design of the collar 210 of the present disclosure can potentially allow for closing the valve 220 after it has been opened. This may be beneficial in cases were certain zones in a multi-zone well begin producing water, or some other unwanted fluids. If the zones that produce the water can be located, the collars associated with that zone can be closed to prevent the undesired fluid flow from the zone. This can be accomplished by isolating the valve vent hole 214 and then pressuring up to force the valve 220 closed. For example, a straddle tool can be employed similar to the embodiment of FIG. 16, except that the packer 140A can be positioned between the fracture ports 212 and the valve vent holes 214, and the lower packer 140B can be positioned on the far side of the valve vent holes 214 from packer 140A. When the zone between the packers is pressurized, it creates a high pressure at the valve vent holes 214 that forces the sleeve 220 closed. As discussed above, the sleeve 220 may include a collet finger 221 that may help retain the sleeve 220 in its closed position.

Although various embodiments have been shown and described, the disclosure is not so limited and will be understood to include all such modifications and variations as would be apparent to one skilled in the art.

What is claimed is:

1. A wellbore completion, comprising:
    a casing assembly comprising a plurality of casing lengths and at least one collar positioned so as to couple the casing lengths,
    wherein the at least one collar comprises,
    a tubular body having an inner flow path;
    at least one fracture port configured to provide fluid communication between an outer surface of the collar and the inner flow path;
    at least one valve hole within the collar intersecting the fracture port;
    at least one vent hole positioned to provide fluid communication between the valve hole and the inner flow path; and
    at least one valve positioned in the valve hole for opening and closing the fracture port, the valve being configured to open when a pressure differential is created between the fracture port and the valve vent hole.

2. The wellbore completion of claim 1, wherein the at least one valve hole is an annulus.

3. The wellbore completion of claim 2, wherein the at least one valve is a sleeve movable within the annulus.

4. The wellbore completion of claim 3, wherein the sleeve further comprises a collet finger adapted to selectively engage a recess on the tubular body.

5. The wellbore completion of claim 2, wherein the annulus encompasses a perimeter of the tubular body.

6. The wellbore completion of claim 1, wherein the valve is a longitudinal rod.

7. The wellbore completion of claim 1, further comprising a plurality of centralizers extending out from the tubular body.

8. The wellbore completion of claim 7, wherein the at least one fracture port extends through the centralizers.

9. The wellbore completion of claim 8, wherein the at least one valve hole is positioned longitudinally in the centralizers.

10. The wellbore completion of claim 1, further comprising a bottom hole assembly positioned in the casing assembly, the bottom hole assembly comprising a packer positioned between the at least one fracture port and the at least one valve vent hole.

11. A collar configured to connect wellbore casing lengths, the collar comprising:
    a mandrel having an inner flow path, an exterior surface, at least one inner fracture port, and at least one valve vent hole;
    a housing connected to the exterior surface of the mandrel, the housing having at least one outer fracture port through the housing;

an annulus between the exterior surface of the mandrel and the housing, the annulus permits fluid communication between the inner fracture port and the outer fracture port, and wherein the valve vent hole is configured to permit fluid communication between the inner flow path and the annulus; and a valve positioned within the annulus, the valve moveable between an open position that permits fluid communication between the inner fracture port and the outer fracture port and a closed position that prevents fluid communication between the inner fracture port and the outer fracture port.

12. The collar of claim 11, wherein the valve is configured to move between the open and closed positions when a pressure differential is created between the fracture port and the valve vent hole.

13. The collar of claim 11, wherein the valve further comprises a sleeve that encircles a perimeter of the mandrel.

14. The collar of claim 11, wherein the housing further comprises at least one fill port adapted for the injection of grease into the annulus.

15. The collar of claim 11, wherein the housing comprises a valve housing sealingly connected to a vent housing.

16. The collar of claim 11, wherein the mandrel further comprises a burstable device positioned within the valve vent hole to selectively prevent fluid communication between the inner flow path and the annulus.

17. The collar of claim 11 further comprising a cement inhibiting substance within the annulus.

18. The collar of claim 11, wherein the mandrel further comprises a plurality of valve vent holes, wherein one of the valve vent holes has a reduced diameter in relation to the other valve vent holes.

19. The collar of claim 18 further comprising a burstable device positioned within each of the valve vent holes except the valve vent hole having a reduced diameter.

20. The collar of claim 19, wherein the burstable devices selectively prevent fluid communication through the valve vent hole between the inner flow path and the annulus.

21. The collar of claim 18, wherein the mandrel further comprises at least one secondary valve vent hole.

22. A method for completing a hydrocarbon producing wellhole, comprising:
applying a pressure differential to open a first fracture port of a casing assembly, the casing assembly comprising a plurality of casing lengths and one or more collars positioned so as to couple together the casing lengths, wherein a first collar of the one or more collars comprises a plurality of apertures, at least one of the plurality of apertures on the first collar being the first fracture port configured to open and close by applying a pressure differential between two apertures on the first collar;
fracturing a well formation by flowing fracturing fluid through the first fracture port; and
running coiled tubing into the wellhole prior to fracturing and subsequently fracturing while the coiled tubing is in the wellhole, wherein the pressure differential applied exceeds the pressure required to fracture the well formation.

23. The method of claim 22 further comprising applying a pressure differential to open a second fracture port, wherein a second collar of the one or more collars comprises a second plurality of apertures, at least one of the apertures of the second collar being the second fracture port configured to open and close by applying a pressure differential between two apertures on the second collar.

24. The method of claim 23 further comprising fracturing a well formation by flowing fracturing fluid through the second fracture port.

25. The method of claim 24, wherein the well formation is fractured through the first fracture port and fractured through the second fracture port on a single trip of coiled tubing.

26. The method of claim 23, wherein the second fracture port is configured to open and close by applying a pressure differential between the second fracture port and another aperture on the second collar.

27. The method of claim 22, wherein the first fracture port is configured to open and close by applying a pressure differential between the first fracture port and another aperture on the first collar.

28. The method of claim 22 further comprising positioning the casing assembly in the wellhole.

29. The method of claim 22, further comprising a bottom hole assembly attached to the coiled tubing, the bottom hole assembly being positioned proximate a fracture port through which fracturing fluid is pumped.

30. The method of claim 22, wherein the hydrocarbon producing well is a multi-zone well.

31. The method of claim 22, wherein the first fracture port comprises a valve capable of moving between an open position and a closed position, wherein the valve allows fluid communication through the first fracture port in the open position and inhibits fluid flow through the first fracture port in the closed position, the first fracture port being closed while running the coiled tubing into the wellhole.

32. The method of claim 31, wherein the first collar is positioned in a first zone of the wellhole and a second collar is positioned in a second zone of the wellhole.

33. The method of claim 32, wherein fracturing comprises moving a valve of the first collar from the closed position to the open position and then fracturing the first zone.

34. The method of claim 33, wherein after the first zone is fractured, moving a valve of the second collar from the closed position to the open position and then fracturing the second zone.

35. The method of claim 22, further comprising applying a pressure differential between the first fracture port and another aperture on the first collar to close the first fracture port after fracturing the wellhole is completed.

36. A system for use in fracturing a well formation, the system comprising:
a first casing segment having an inner flow path and a plurality of centralizers, the centralizers being configured to substantially center the first casing segment within a wellbore and at least one of the centralizers being adjacent to a first zone of a well formation;
a first fracture port that extends through the centralizer adjacent to the first zone, wherein the first fracture port is adapted to permit fluid communication between the inner flow path of the first casing segment and first zone of the well formation; and
a valve configured to selectively open and close the first fracture port upon the application of a pressure differential between the first fracture port and another aperture on the first casing segment.

37. The system of claim 36 further comprising:
a second casing segment having an inner flow path and a plurality of centralizers, the centralizers being configured to substantially center the second casing segment within the wellbore and at least one of the centralizers being adjacent to a second zone of the well formation;
a second fracture port that extends through the centralizer adjacent to the second zone, wherein the second fracture port is adapted to permit fluid communication between the inner flow path of the second casing segment and the second zone of the well formation.

38. The system of claim 37 further comprising a first valve configured to selectively open and close the first fracture port upon the application of a pressure differential within the first casing segment and a second valve configured to selectively open and close the second fracture port upon the application of a pressure differential within the second casing segment.

39. The system of claim 36 further comprising a burstable device positioned within the first fracture port to selectively prevent fluid communication into the first fracture port from the wellbore.

40. A method for completing a hydrocarbon producing wellhole, comprising:
- running a bottom hole assembly attached to an end of a coiled tubing string into a casing assembly, the bottom hole assembly including a packer seal surrounding at least a portion of the bottom hole assembly, wherein the casing assembly comprising a plurality of casing lengths and at least one collar having a fracture port configured to open by application of a pressure differential;
- positioning the packer seal of the bottom hole assembly proximate to the fracture port of the at least one collar;
- energizing the packer seal of the bottom hole assembly to create a seal in the casing assembly;
- pumping fluid down an annulus between the coiled tubing string and the casing assembly to create a pressure differential across the packer seal opening the fracture port of the collar; and
- fracturing a well formation by flowing fracturing fluid through the fracture port.

* * * * *

UNITED STATES PATENT AND TRADEMARK OFFICE
CERTIFICATE OF CORRECTION

Page 1 of 1

PATENT NO. : 8,613,321 B2
APPLICATION NO. : 12/842099
DATED : December 24, 2013
INVENTOR(S) : Ravensbergen et al.

It is certified that error appears in the above-identified patent and that said Letters Patent is hereby corrected as shown below:

In the Claims

Claim 1, Col. 16, Line 20-37, should read

1. A wellbore completion, comprising:
   a casing assembly comprising a plurality of casing lengths and at least one collar positioned so as to couple the casing lengths,
      wherein the at least one collar comprises,
      a tubular body having an inner flow path;
      at least one fracture port configured to provide fluid communication between an outer surface of the collar and the inner flow path;
      at least one valve hole within the collar intersecting the fracture port;
      at least one valve vent hole positioned to provide fluid communication between the valve hole and the inner flow path; and
      at least one valve positioned in the valve hole for opening and closing the fracture port, the valve being configured to open when a pressure differential is created between the fracture port and the valve vent hole.

Signed and Sealed this
Twenty-first Day of July, 2015

Michelle K. Lee
*Director of the United States Patent and Trademark Office*